United States Patent
Bystrov et al.

(10) Patent No.: US 7,684,604 B2
(45) Date of Patent: Mar. 23, 2010

(54) APPARATUS AND METHOD FOR PLANNING MAGNETIC RESONANCE IMAGING

(75) Inventors: Daniel Bystrov, Hamburg (DE); Thomas Netsch, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 818 days.

(21) Appl. No.: 11/568,121

(22) PCT Filed: Mar. 30, 2005

(86) PCT No.: PCT/IB2005/051068
§ 371 (c)(1),
(2), (4) Date: Oct. 20, 2006

(87) PCT Pub. No.: WO2005/102160
PCT Pub. Date: Nov. 3, 2005

(65) Prior Publication Data
US 2009/0154783 A1 Jun. 18, 2009

Related U.S. Application Data (60) Provisional application No. 60/565,385, filed on Apr. 26, 2004.

(51) Int. Cl.
*G06K 9/00* (2006.01)
*A61B 6/00* (2006.01)
(52) U.S. Cl. .................... 382/131; 382/299; 378/19
(58) Field of Classification Search .......... 382/100, 382/128, 129, 130, 131, 132, 133, 134, 154, 382/168, 181, 203, 216, 232, 254, 274, 276, 382/291, 193, 295, 299, 305, 312; 378/19, 378/4; 600/410, 407; 324/309
See application file for complete search history.

(56) References Cited

U.S. PATENT DOCUMENTS

| 5,514,957 | A | * | 5/1996 | Tatebayashi | 324/309 |
| 6,366,638 | B1 | * | 4/2002 | Hsieh et al. | 378/19 |
| 6,725,077 | B1 | * | 4/2004 | Balloni et al. | 600/410 |

(Continued)

FOREIGN PATENT DOCUMENTS

EP  1 220 153 A2  7/2002

OTHER PUBLICATIONS

Lelieveldt, B.P.F., et al.; Automated Observer-independent Acquisition of Cardiac Short-Axis MR Images: A Pilot Study; 2001; Radiology; 221(2)537-542.

*Primary Examiner*—Seyed Azarian (57) ABSTRACT

A diagnostic imaging system includes a magnetic resonance imaging scanner (10) for imaging an organ of interest, a reformatting processor (70) for constructing reformatted images corresponding to a scout image in different coordinate systems, and a graphical user interface (62) for displaying acquired images and reformatted images to an associated user. An imaging processor (60) causes the scanner (10) to acquire a base sparse scout image of an organ of interest in a standard coordinate system, causes the reformatting processor (70) to generate one or more reformatted images from the sparse scout image in coordinate systems other than the standard coordinate system, determines a diagnostic imaging coordinate system aligned with the organ of interest using the base sparse scout image and the one or more reformatted images, and causes the scanner (10) to acquire one or more diagnostic images of the organ of interest in the diagnostic imaging coordinate system.

20 Claims, 4 Drawing Sheets

U.S. PATENT DOCUMENTS

| | | |
|---|---|---|
| 6,898,302 B1 * | 5/2005 | Brummer .................... 382/131 |
| 7,596,255 B2 * | 9/2009 | Mathew et al. .............. 382/130 |
| 2002/0156359 A1 * | 10/2002 | Knoplioch et al. .......... 600/407 |
| 2003/0055328 A1 * | 3/2003 | Paladini ...................... 600/407 |
| 2005/0165300 A1 | 7/2005 | Haselhoff et al. |

* cited by examiner

FIG 4

APPARATUS AND METHOD FOR PLANNING MAGNETIC RESONANCE IMAGING

CROSS REFERENCE TO RELATED APPLICATIONS

This application claims the benefit of U.S. provisional application Ser. No. 60/564,385 filed Apr. 26, 2004, which is incorporated by reference.

The following relates to the magnetic resonance arts. It finds particular application in cardiac magnetic resonance imaging, and will be described with particular reference thereto. However, it also finds application in other types of magnetic resonance imaging such as brain imaging, and in other imaging modalities.

One advantage of magnetic resonance imaging is the ability to acquire image slices at arbitrary spatial orientations. In contrast, other imaging modalities such as computed tomography typically are configured to acquire data in a fixed coordinate system, such as axial-sagittal-coronal coordinates, and are not readily adapted to acquire imaging data in other coordinate systems. Extracting a slice other than an axial, sagittal, or coronal slice from such an image requires additional image processing, typically including interpolation of reconstructed voxels along inclined planes, which is computationally intensive and can produce image artifacts.

In the case of cardiac imaging, it is often advantageous to acquire image slices transverse to a long axis of the heart running from the apex to the valve plane, or to acquire image slices transverse to a short axis of the heart. In the typical case of a prone patient lying in a horizontal bore scanner, the principal axes of the heart are substantially inclined to the axial direction. Other organs of interest, such as the brain, also may have inherent anatomical geometries that are not commensurate with the conventional axial, sagittal, and coronal anatomical planes.

In planning a diagnostic magnetic resonance imaging session, it is common to perform several so-called "scout" scans of the heart or other organ of interest. In one common procedure for preparing a cardiac scan, a first scout scan is acquired including 10-20 axial slices in each of the axial, sagittal, and coronal directions. The slices of the scout scan are sparsely distributed across the anticipated region of interest with gaps between the slices. The radiologist identifies the projection of a long axis of the heart in the sparse scout scan; however, because the data set is sparse corresponding to a low resolution image, the identified projection may be approximate. A second sparse scout scan is acquired aligned with the identified long cardiac axis. This second acquired sparse scout scan is used to identify the valve plane. A third sparse scout scan may be acquired to identify a short axis of the heart.

Existing methods for planning diagnostic cardiac magnetic resonance imaging have certain disadvantages. Acquisition of several scout scans takes time and exposes the patient to magnetic field gradients and radio frequency excitations. Also, the radiologist is required to make several decisions regarding the orientation of the long axis or other anatomical orientation axis.

Some efforts have been expended toward automating the pre-scan planning. In one approach, an automated algorithm is used to determine a long axis or other anatomical axis in the scout images. Such automation relieves the radiologist from making such selections manually, but introduces other problems. The anatomical alignment identified by the automated process may be less than optimal. As a consequence, the radiologist must either acquire additional sparse scout images to check the alignment and, if necessary, to manually "fine-tune" the anatomical alignment, or perform the diagnostic imaging in anatomical coordinates that may not be optimal. Moreover, the automated process is interrupted for additional data acquisition each time a scout image having a new or updated orientation is called for by the automated process.

Higher resolution scout images can be employed to increase the accuracy of axis selection and reduce the number of optimization iterations. However, such higher resolution scout images take longer to acquire and expose the imaging subject to higher levels of magnetic field gradients and radio frequency excitations. A tradeoff between scout image resolution and number of iterations is thus involved.

The present invention contemplates an improved apparatus and method that overcomes the aforementioned limitations and others.

According to one aspect, a magnetic resonance imaging method is provided. A sparse scout image having low resolution is acquired. The sparse scout image is reformatted to generate one or more reformatted images having different coordinate systems. A diagnostic imaging coordinate system is determined based on the sparse scout image and the one or more reformatted images. One or more diagnostic images are acquired using space-encoding magnetic field gradients aligned with respect to the diagnostic imaging coordinate system.

According to another aspect, a diagnostic imaging system is disclosed. A magnetic resonance imaging scanner acquires images. A reformatting processor receives a sparse scout image and constructing a reformatted image corresponding to the scout image in a different coordinate system. A graphical user interface displays acquired images and reformatted images to an associated user. A diagnostic imaging processor performs a method including: causing the magnetic resonance imaging scanner to acquire a base sparse scout image of an organ of interest in a standard coordinate system; causing the reformatting processor to reformat the base sparse scout image to generate one or more reformatted images in coordinate systems other than the standard coordinate system; determining a diagnostic imaging coordinate system aligned with the organ of interest using the base sparse scout image and the one or more reformatted images; and causing the magnetic resonance imaging scanner to acquire one or more diagnostic images of the organ of interest in the diagnostic imaging coordinate system.

According to yet another aspect, a diagnostic imaging system is disclosed. A software algorithm or routine is provided for causing a magnetic resonance imaging scanner to acquire a base sparse scout image of an organ of interest in a standard coordinate system. A software algorithm or routine is provided for reformatting the base sparse scout image to generate one or more reformatted images in coordinate systems other than the standard coordinate system. A software algorithm or routine is provided for determining a diagnostic imaging coordinate system aligned with the organ of interest using the base sparse scout image and the one or more reformatted images. A graphical user interface is provided for displaying acquired images and reformatted images to an associated user. A software algorithm or routine is provided for causing the magnetic resonance imaging scanner to acquire one or more diagnostic images of the organ of interest in the diagnostic imaging coordinate system.

One advantage resides in more rapid planning of diagnostic imaging procedures.

Another advantage resides in consequent improved patient throughput in a magnetic resonance imaging facility.

Yet another advantage resides in more accurate planning of diagnostic imaging.

Still yet another advantage resides in providing a preview of the final scan orientation before beginning the diagnostic imaging session.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 1:
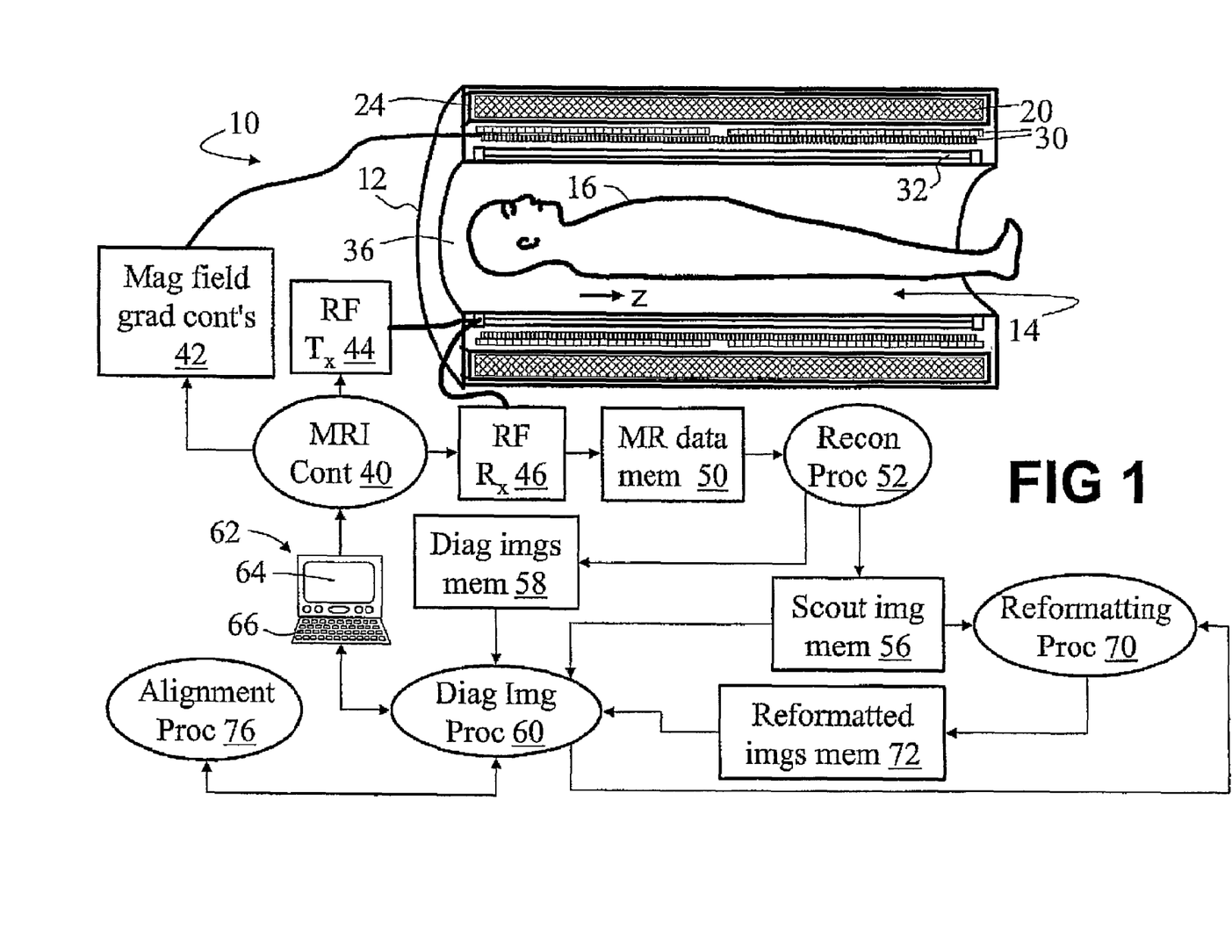
FIG. 1 diagrammatically shows a magnetic resonance imaging system with a diagnostic imaging planning system.

With reference to FIG. 1, a magnetic resonance imaging scanner 10 includes a housing 12 defining a generally cylindrical scanner bore 14 inside of which an associated imaging subject 16 is disposed. Main magnetic field coils 20 are disposed inside the housing 12, and produce a temporally constant $B_0$ magnetic field directed generally along a direction, designated the z-direction in FIG. 1, which is substantially parallel to a central axis of the scanner bore 14.

The housing 12 also houses or supports magnetic field gradient-generating structures, such as magnetic field gradient coils 30, for selectively producing magnetic field gradients parallel to the z-direction, transverse to the z-direction, or along other selected directions. The housing 12 further houses or supports a radio frequency body coil 32 for selectively exciting magnetic resonances. Specifically, the radio frequency body coil 32 produces a radio frequency $B_1$ magnetic field transverse to the temporally constant $B_0$ magnetic field. The radio frequency $B_1$ magnetic field is generated at the Larmor frequency for exciting a nuclear magnetic resonance. In the illustrated embodiment, the coil 32 is a whole body birdcage coil; however, a local coil, a whole-body TEM coil, or other radio frequency coil can be used for exciting magnetic resonance in the subject 16. The housing 12 typically includes a cosmetic inner liner 36 inside the birdcage coil 32 defining the scanner bore 14.

During imaging, the main magnetic field coils 20 produce the temporally constant $B_0$ magnetic field parallel to the z-direction in the bore 14. A magnetic resonance imaging controller 40 operates magnetic field gradient controllers 42 to selectively energize the magnetic field gradient coils 30, and operates a radio frequency transmitter 44 coupled to the radio frequency coil 32 to selectively energize the radio frequency coil 32. By selectively operating the magnetic field gradient coils 30 and the radio frequency coil 32, magnetic resonance is generated and spatially encoded in at least a portion of a region of interest of the imaging subject 16. By applying selected magnetic field gradients via the gradient coils 30, a selected k-space trajectory is traversed during acquisition of magnetic resonance signals, such as a Cartesian trajectory, a plurality of radial trajectories, or a spiral trajectory.

The radio frequency coil 32 is also coupled to a radio frequency receiver 46 for receiving magnetic resonance signals. Alternatively, a separate radio frequency receive coil or coil array is provided, such as a surface coil or coils array. The receiver 46 acquires magnetic resonance sampling data that are stored in a magnetic resonance data memory 50. The magnetic resonance data are reconstructed by a reconstruction processor 52 into one or more reconstructed images. In the case of k-space sampling data, a Fourier transform-based reconstruction algorithm can be employed. Other reconstruction algorithms, such as a filtered backprojection-based reconstruction, can also be used depending upon the format of the magnetic resonance imaging data.

The described magnetic resonance imaging scanner 10 is an example. The diagnostic image planning methods and apparatus described herein, and their equivalents, can be employed in conjunction with substantially any type of magnetic resonance imaging scanner, including vertical magnet scanners, open magnet scanners, short bore scanners, and so forth.

The reconstructed image generated by the reconstruction processor 52 is stored in an image memory. Before performing diagnostic imaging, a sparse scout image having low resolution is acquired in a region of interest containing an organ of interest, such as a heart, brain, or other organ of interest. In one example, the slices of the sparse scout image are 1-3 millimeters thick, but are spaced out at 1 centimeter intervals. The sparse scout image is stored in a scout image memory 56, and is used to determine scan geometry and scan parameters for subsequent diagnostic imaging. Subsequently, diagnostic imaging data are acquired and reconstructed by the reconstruction processor 52 into one or more diagnostic images that are stored in a diagnostic images memory 58.

A diagnostic imaging processor 60 controls the overall diagnostic imaging session. At various times during the diagnostic imaging session, selected images from the scout image memory 56 or from the diagnostic images memory 58 are retrieved by the diagnostic imaging processor 60 and transmitted to a graphical user interface 62 (GUI) for display to a radiologist, technician, or other associated user. The images can also be transmitted over a local intranet or the Internet, viewed, stored, manipulated, or so forth. The graphical user interface 62 includes a graphical display 64 for displaying images and other information, and one or more user input devices such as a keyboard 66, a mouse or other pointing device (not shown), or the like. In preferred embodiments, the radiologist, technician, or other user can make certain inputs such as selecting landmarks in an image using the keyboard 66, a pointing device, or the like to indicate a position in an image displayed on the display 64. The display 64 may also, however, include non-graphical content, such as numerical input fields, text messages, numerical indicators, or the like, for interfacing with the radiologist, technician, or other associated user.

Preferred embodiments of diagnostic imaging planning procedures are now described in greater detail. The planning is performed using a sparse scout image acquired by the magnetic resonance imaging scanner 10 and stored in the scout image memory 56. The scout image is sparse in that it is a low resolution image. A typical sparse scout image, for example, includes around 5-20 axial slices, 5-20 sagittal slices, and 5-20 coronal slices. It will be appreciated that such a sparse image generally has insufficient resolution to perform image rotation. Nonetheless, preferably the entire planning is performed using a single sparse scout image.

In order to manipulate the single sparse scout image to provide views along geometries other than the conventional axial-sagittal-coronal coordinate system, a reformatting processor 70 reformats the sparse scout image to generate one or more reformatted images having different coordinate systems. The reformatted images are stored in a reformatted images memory 72. The reformatted images are derived from the single acquired sparse scout image; they are not separately acquired images.

The reformatting is used to determine a diagnostic imaging coordinate system which is preferably an anatomically significant coordinate system related to the organ of interest. For example, in cardiac imaging the reformatting be used to determine a coordinate system aligned with long and/or short principal axes of the heart. The anatomically significant diagnostic imaging coordinate system is selected manually by the radiologist, technician, or other associated user by selecting landmarks in the sparse scout image and in reformatted images via the graphical user interface 62. The landmarks can represent anatomical points, principal anatomical axes, angulations, translational offsets, a cardiac valve plane or other anatomical feature, or the like. In some cases, a landmark may be derived from one or more user selections. For example, an axis or angulation landmark can be identified by selecting two or more point landmarks lying on the axis. Similarly, a plane landmark can be identified by selecting three or more non-linear points lying in the plane, or by selecting two non-coincident lines lying in the plane. Instead of manually determining the alignment coordinates, an automatic alignment processor 76 preferably determines the anatomically significant diagnostic imaging coordinate system by automated analysis of the sparse scout image and one or more reformatted images.

Figure 2:
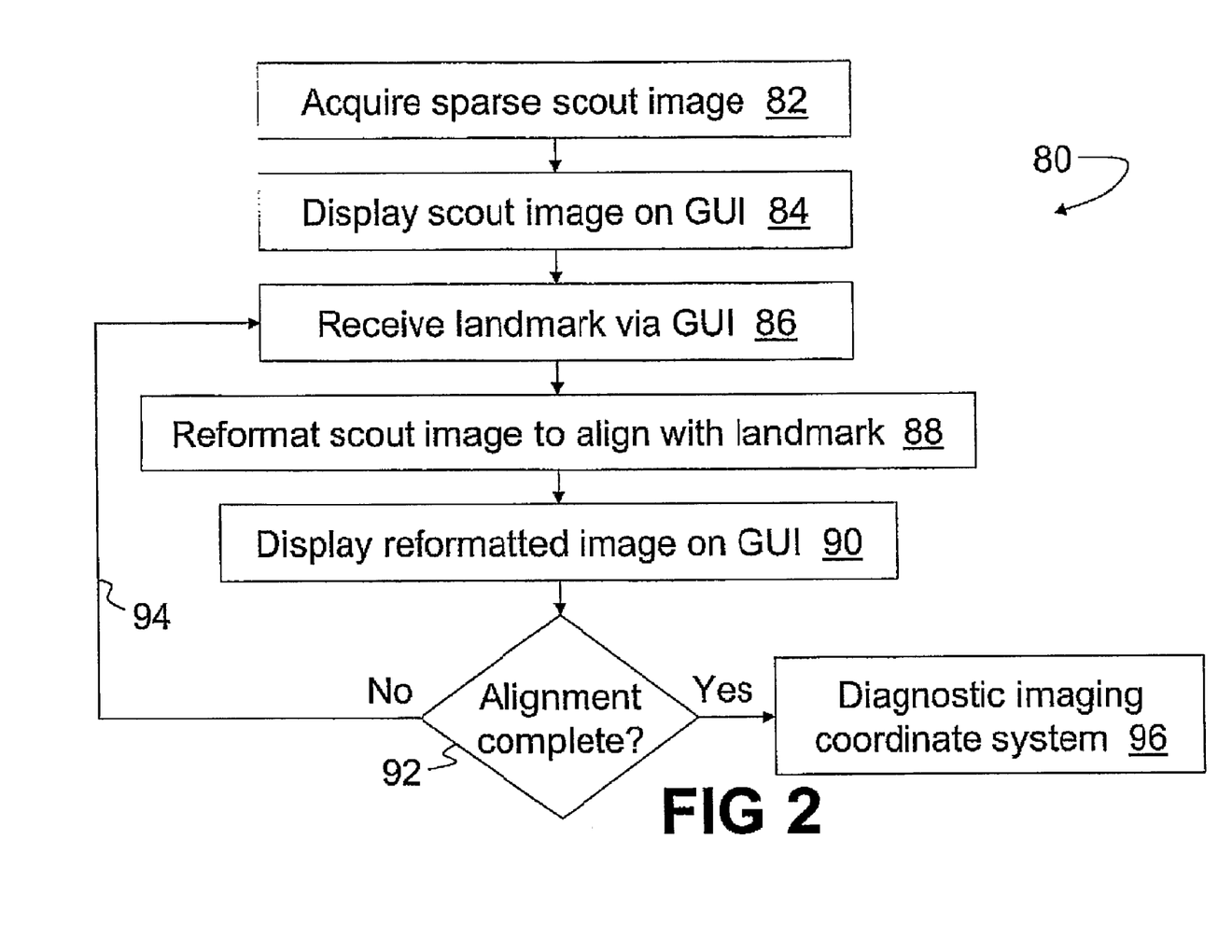
FIG. 2 diagrams an example manual planning procedure performed by the diagnostic imaging planning system of FIG. 1.
Figure 3:
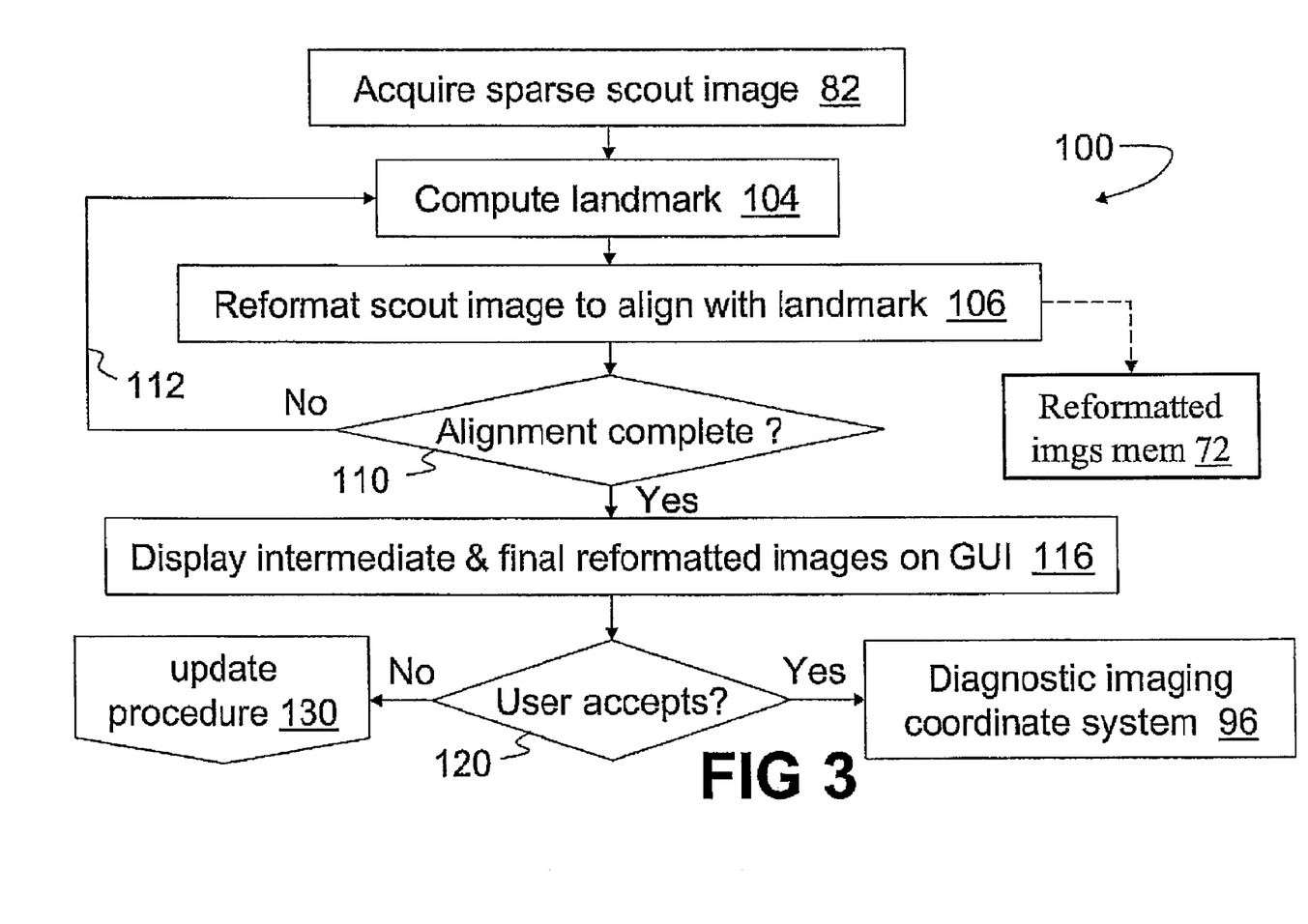
FIG. 3 diagrams an example automated planning procedure performed by the diagnostic imaging planning system of FIG. 1.

Having described the components of the diagnostic imaging planning system, specific example cardiac planning procedures are now described with continuing reference to FIG. 1 and with further reference to FIGS. 2 and 3.

With continuing reference to FIG. 1 and with further reference to FIG. 2, a manual planning procedure 80 is described. In acquisition process operation 82, a sparse scout image is acquired by the magnetic resonance imaging scanner 10 and stored in the scout image memory 56. For example, the scout image may include fifteen axial slices, ten sagittal slices, and ten coronal slices. Optionally, rather than using an axial-sagittal-coronal coordinate system, the initial sparse scout scan can have an oblique standard coordinate system selected based on a priori knowledge of the orientation of the axes of interest in a typical patient. The volume imaged by the sparse scout image is selected to at least encompass the expected location of the heart. The acquired sparse scout image is displayed on the graphical user interface 62 in display process operation 84. The imaged cardiac muscle is generally not well aligned with the conventional axial-sagittal-coronal coordinate system used in acquiring the sparse scout image. For example, the long axis of the heart is usually significantly angularly offset from the axial direction.

Consequently, the diagnostic imaging is advantageously performed in an anatomically significant diagnostic imaging coordinate system that is generally different from the axial-sagittal-coronal coordinate system. For example, the imaging may be performed with slices transverse to the long axis of the heart, or transverse to a short axis of the heart.

In order to identify the desired anatomically significant coordinate system for diagnostic imaging, the radiologist, technician, or other associated user identifies one or more anatomically significant landmarks in the sparse scout image displayed on the graphical user interface 62 in user input process operation 86. For example, landmarks lying on the long axis of the heart are identified. For planning a cardiac imaging session, landmarks are typically selected to identify angulation and center offsets of the imaged heart. For example, in one typical approach for cardiac imaging, landmarks are selected to identify an angulation of the long axis respective to the axial-sagittal-coronal coordinate system. The identified angulation defines an updated coordinate system different from the axial-sagittal-coronal coordinate system. The reformatting processor 70 in invoked to reformat the sparse scout image in the updated coordinate system in reformatting process operation 88, and the reformatted image is displayed on the graphical user interface 62 in display process operation 90.

The reformatting processor 70 performs the reformatting by defining a set of voxel positions in the updated coordinate system, and computing a voxel value at each voxel position by performing a distance-weighted interpolation of neighboring voxels of the sparse scout image. The reformatted image is not a newly acquired image; rather, it is a reformatted version of the original sparse scout image.

At a decision process operation 92, the decision is made as to whether the anatomically significant diagnostic imaging coordinate system has been fully identified. Typically, planning for cardiac imaging includes three distinct selections of landmarks to uniquely identify a long axis and a short axis of the heart. Hence, in an iteration process operation 94 (represented in FIG. 2 by a feedback flow arrow) the graphical user interface 62 allows the radiologist, technician, or other associated user to select a second set of one or more landmarks in input process operation 86, this time in the reformatted image, to further specify the unique anatomically significant coordinate system. A second reformatted image using the further refined coordinate system is computed by the reformatting processor 70 in the second iteration of reformatting process operation 88, and the second reformatted image is display on the graphical user interface 62 in the second iteration of the display process operation 90. A third iteration is optionally performed to define the short axis view of the heart. The final anatomically significant diagnostic imaging coordinate system 96 is thus determined.

Advantageously, the entire planning procedure 80 is performed using a single sparse scout image acquired in the acquisition process operation 82. Subsequent views of the organ of interest used in the planning procedure are derived by image processing from this single sparse scout image using the reformatting processor 70. Because the sparse scout image is low resolution, the reformatting generally cannot involve a simple rotation operation. Rather, the reformatting is performed by defining a set of voxel positions in the updated coordinate system, and computing a voxel value at each voxel position by distance-weighted interpolation of neighboring voxels of the sparse scout image.

Although only a single sparse scout image is preferably employed, in some embodiments the user interfacing mimics existing planning user interfaces which employ multiple acquired sparse scout images. The planning procedure 80 is made compatible with such existing user interfaces by substituting the reformatted images for the subsequent sparse scout image acquisitions used in the existing planning. In such embodiments, the radiologist, technician, or other associated user advantageously does not need to learn a new user interface.

In addition to identifying anatomically significant coordinates for the diagnostic imaging, the reformatted images can also be used to determine other scan parameters. For example, the reformatted image can be used to define a shim volume over which active shimming is performed.

With continuing reference to FIG. 1 and with further reference to FIG. 3, an automated planning procedure 100 is described. The single sparse scout image is acquired in process operation 82 similarly to the manual planning. Optionally, rather than using an axial-sagittal-coronal coordinate system, the initial sparse scout scan can have an oblique standard coordinate system selected based on a priori knowledge of the orientation of the axes of interest in a typical patient. Rather than having the radiologist, technician, or other associated user make the landmarks selection, however, in the automated planning procedure 100 one or landmarks are computed automatically by the alignment processor 76 in process operation 104.

Automated procedures are known in the art for computing landmarks in cardiac images having particular coordinate systems. Thus, for example, automated procedures are known for identifying the angulation and center correction for the long axis in an image having the conventional axial-sagittal-coronal coordinate system, and for further refining the coordinate system using subsequent views. Similar automated landmarks computations are also known or can be readily developed for aligning other organs of interest. The process operation 104 can be implemented using such automated procedures to perform the landmark computation process operation 104.

Rather than acquiring a new image using the coordinate system aligned with the landmark or landmarks identified in process operation 104, as has been done in the past, in the automated planning procedure 100 the image with the coordinate system aligned with the landmark or landmarks is derived mathematically by the reformatting processor 70 in reformatting process operation 106. The reformatted image is preferably stored in the reformatted images memory 72. Similarly to the manual procedure 80, at a decision process operation 110, a decision is then made as to whether the anatomically significant diagnostic imaging coordinate system has been fully identified. Typically, two or three iterations are required to fully define the anatomically significant coordinate system. Thus, in an iteration process operation 112 (represented in FIG. 3 by a feedback flow arrow) the procedure repeats the automated landmark identification 104 and the image reformatting 106 for each refinement of the coordinate system. The final reformatted image after the iterating should correspond to the anatomically significant diagnostic imaging coordinates.

However, automated planning sometimes produces diagnostic imaging coordinates that are not well aligned with the organ of interest. To address this possibility, the final reformatted images of each of the intermediate steps are displayed on the graphical user interface 62 in display process operation 116. The radiologist, technician, or other associated user in a manual decision process operation 120 decides if, in the cardiac example, the long axis was properly selected, whether the valve plane was properly identified, and so forth. Based on whether the intermediate coordinate selections are acceptable, the user decides whether or not to accept the automatically determined coordinates system. If accepted, then the automatically determined coordinates system serves as the diagnostic imaging coordinate system 96.

If, however, at the decision process operation 120 the radiologist, technician, or other associated user decides that the automatically determined coordinates need to be improved upon, then the automated planning procedure 100 transfers control to an update procedure 130. In the automated planning procedure 100, each computed landmark or set of landmarks is used to construct an intermediate reformatted image aligned with respect to that landmark or landmarks. Thus, an ordered set of landmarks, such as an ordered set of principal axes, is determined in which the ordering corresponds to the order in which the landmarks were input or determined. The corresponding set of reformatted images constructed during the automated planning are preferably stored in the reformatted images memory 72. Accordingly, the radiologist, technician, or other associated user can access and view the intermediate reformatted images as well as the resulting automatically determined diagnostic coordinate system, and can instigate corrective action at any point in the automated procedure.

Figure 4:
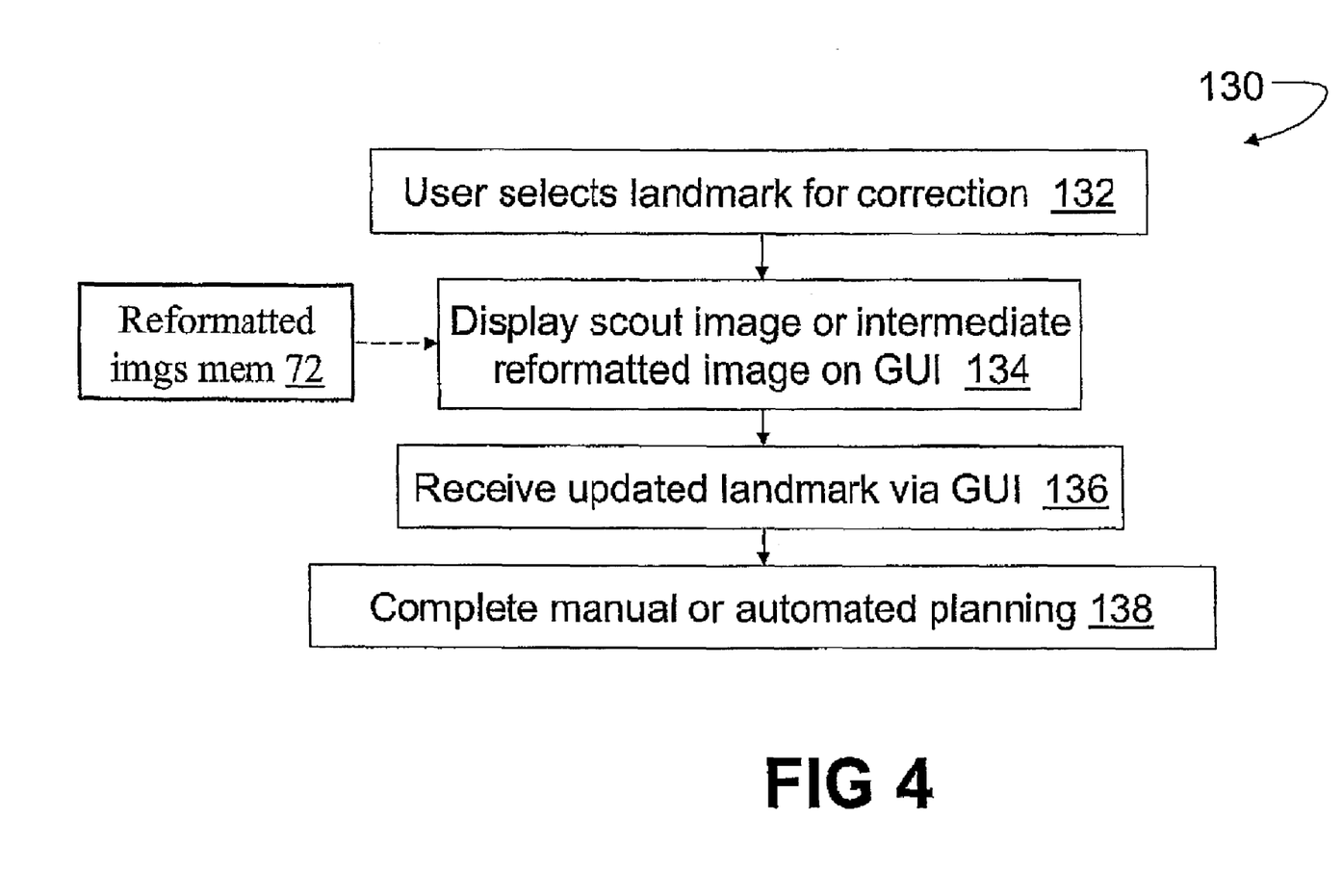
FIG. 4 diagrams an example planning update procedure performed by the diagnostic imaging planning system of FIG. 1 to correct or update the diagnostic imaging coordinate system determined by the automated process of FIG. 3.

With continuing reference to FIG. 1 and with further reference to FIG. 4, the correction or update procedure 130 begins by the radiologist, technician, or other associated user selecting a landmark, such as a principal axis, angulation, center offset, or the like, for correction or update in an input process operation 132. The selection is suitably made using the graphical user interface 62, for example, by selecting the problematic intermediate reformatted image from amongst the reformatted images displayed in the display process operation 116 (see FIG. 3). The corresponding reformatted image in which the selected problematic landmark was identified is recalled from the reformatted images memory 72 and is displayed on the graphical user interface 62 in display process operation 134. An updated landmark value or landmark values is identified by the radiologist, technician, or other associated user via the graphical user interface 62 in an input process operation 136. In process operation 138, either the manual planning 80 (diagrammed in FIG. 2) or the automated planning procedure 100 (diagrammed in FIG. 3) is performed using the landmarks preceding the selected landmark in the ordering and the updated value of the selected landmark.

As an example, the automated planning procedure 100 may perform a cardiac planning procedure that includes identifying the following ordered set of landmarks: (i) a long axis of the heart; (ii) a valve plane of the heart; and (iii) a short axis of the heart. That is, in the first iteration the long axis of the heart is identified in the sparse scout image and a first reformatted image is constructed aligned with the long axis is determined; in the second iteration the valve plane is identified in the first reformatted image and a second reformatted image is constructed aligned with both the long axis and the valve plane; and in a third iteration the short axis is identified and a third reformatted image is constructed aligned with the long and short axes and the valve plane. The intermediate and final reformatted images are displayed to the radiologist, technician, or other associated user in the display process operation 116. In the decision 120, the user may decide to perform the update procedure 130 manually for one or more iterations because, for example, the identified valve plane may not be well selected by the automated procedure 100.

In the update procedure 130, an updated valve plane is selected via process operations 132, 134, 136. Using this updated valve plane landmark, in process operation 138 the automated procedure 100 repeats the construction of the second reformatted image and the entire third iteration in which the third ordered landmark, namely the short axis, is determined. The updated images are presented for review in the display process operation 116. Rather than repeating the automated processing 100, the process operation 138 can instead transfer control to the manual procedure 80 so that the radiologist, technician, or other associated user can manually determine an updated value of the short axis.

With returning reference to FIG. 3, the entire automated planning procedure 100 is performed using a single sparse scout image acquired in the acquisition process operation 82. Subsequent views of the organ of interest used in the planning procedure are derived by image processing from this single sparse scout image using the reformatting processor 70. Accordingly, the procedure flow is continuous; there are no interruptions during which updated images are physically acquired by the scanner 10. Moreover, the reformatting allows manual correction of the automatically generated coordinates via the update procedure 130, again without interruptions for additional data acquisition.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A magnetic resonance imaging method comprising:
    acquiring a sparse scout image having low resolution;
    reformatting the sparse scout image to generate one or more reformatted images having different coordinate systems;
    determining a diagnostic imaging coordinate system based on the sparse scout image and the one or more reformatted images; and
    acquiring one or more diagnostic images using space-encoding magnetic field gradients aligned with respect to the diagnostic imaging coordinate system.

2. The method as set forth in claim 1, wherein the acquiring of the sparse scout image comprises acquiring a single sparse scout image, the acquiring of the single spare scout image comprising:
    acquiring approximately twenty or less axial slices;
    acquiring less than or about twenty coronal slices; and
    acquiring less than or about twenty sagittal slices.

3. The method as set forth in claim 2, wherein the reformatting comprises:
    identifying a set of voxel positions in the different coordinate system; and
    computing a voxel value at each voxel position by performing a distance-weighted interpolation of neighboring voxels of the sparse scout image.

4. The method as set forth in claim 1, wherein the reformatting comprises:
    displaying the sparse scout image to an associated user via a graphical user interface;
    receiving an indication of a first landmark by user interaction with the sparse scout image via the graphical user interface; and
    reformatting the sparse scout image to generate a first reformatted image having a coordinate system aligned with respect to the first landmark.

5. The method as set forth in claim 4, wherein the reformatting further comprises:
    displaying the first reformatted image to the associated user via the graphical user interface;
    receiving an indication of a second landmark by user interaction with the reformatted image via the graphical user interface; and
    reformatting one of the sparse scout image and the first reformatted image to generate a second reformatted image having a coordinate system aligned with the second landmark.

6. The method as set forth in claim 4, wherein the reformatting further comprises:
    displaying the first reformatted image to the associated user via the graphical user interface;
    receiving an indication of a second landmark different from the first landmark by user interaction with the reformatted image via the graphical user interface; and
    reformatting one of the sparse scout image and the first reformatted image to generate a second reformatted image having a coordinate system aligned with both the first and second landmarks.

7. The method as set forth in claim 1, wherein a region of interest of the imaging is the heart, and the reformatting comprises:
    displaying the sparse scout image to an associated user via a graphical user interface;
    receiving an indication via the graphical user interface of a long principal axis of the heart in the sparse scout image;
    reformatting the sparse scout image to generate a first reformatted image having a coordinate system aligned with the long principal axis of the heart;
    displaying the first reformatted image to the associated user via the graphical user interface;
    receiving an indication via the graphical user interface of a short principal axis of the heart in the first reformatted image;
    reformatting one of the sparse scout image and the first reformatted image to generate a second reformatted image having a coordinate system aligned with both the long and short principle axes of the heart; and
    displaying the second reformatted image to the user via the graphical user interface.

8. The method as set forth in claim 1, wherein the reformatting comprises:
    performing an automated analysis of the sparse scout image to determine a first landmark;
    reformatting the sparse scout image to generate a first reformatted image having a coordinate system aligned with the first landmark;
    repeating the automated analysis and reformatting at least once to generate an ordered plurality of reformatted images and a corresponding ordered plurality of determined landmarks starting with the first reformatted image and the first landmark, respectively, each successive one of the ordered plurality of landmarks having a corresponding reformatted image aligned with that landmark and with the previously determined landmarks; and
    displaying the last reformatted image of the ordered plurality of reformatted images to an associated user via a graphical user interface.

9. The method as set forth in claim 8, wherein the reformatting further comprises:
    displaying the ordered plurality of reformatted images on the graphical user interface with the corresponding landmark superimposed thereon; and
    receiving a corrected landmark replacing one of the superimposed landmarks from the associated user via the graphical user interface.

10. The method as set forth in claim 9, wherein the reformatting further comprises:
    repeating the automated analysis and reformatting for each landmark of the ordered plurality of landmarks succeeding the corrected landmark in the ordering, the automated analyses being performed respective to previously determined landmarks including the corrected landmark; and
    displaying the last corrected reformatted image of the ordered plurality of corrected reformatted images to an associated user via a graphical user interface.

11. A diagnostic imaging system comprising:
    a magnetic resonance imaging scanner for acquiring images;

a reformatting processor receiving a sparse scout image and constructing a reformatted image corresponding to the scout image in a different coordinate system;

a graphical user interface for displaying acquired images and reformatted images to an associated user; and a diagnostic imaging processor performing a method including:

causing the magnetic resonance imaging scanner to acquire a base sparse scout image of an organ of interest in a standard coordinate system, causing the reformatting processor to reformat the base sparse scout image to generate one or more reformatted images in coordinate systems other than the standard coordinate system, determining a diagnostic imaging coordinate system aligned with the organ of interest using the base sparse scout image and the one or more reformatted images, and causing the magnetic resonance imaging scanner to acquire one or more diagnostic images of the organ of interest in the diagnostic imaging coordinate system.

12. The diagnostic imaging system as set forth in claim 11, wherein the reformatting processor performs a reformatting method comprising:

identifying a set of voxel positions in the different coordinate system; and computing a voxel value at each voxel position by performing a distance-weighted interpolation of neighboring voxels of the sparse scout image.

13. The diagnostic imaging system as set forth in claim 11, wherein the determining of a diagnostic imaging coordinate system comprises:

(i) causing the graphical user interface to display the base sparse scout image to the associated user;

(ii) receiving an indication of one or more landmarks from the associated user via the graphical user interface;

(iii) causing the reformatting processor to reformat the sparse scout image to generate a first reformatted image having a coordinate system defined by the one or more landmarks;

(iv) causing the graphical user interface to display the first reformatted image to the associated user;

(v) repeating the process operations (i), (ii), (iii), and (iv) at least once to generate a plurality of reformatted images, the coordinate system of the last generated reformatted image being the diagnostic imaging coordinate system.

14. The diagnostic imaging system as set forth in claim 13, wherein the organ of interest is the heart, and the one or more landmarks indicate at least an apex of the heart and a valve plane of the heart.

15. The diagnostic imaging system as set forth in claim 13, wherein the organ of interest is the heart, and the one or more landmarks indicate at least a long axis of the heart and a short axis of the heart.

16. The diagnostic imaging system as set forth in claim 11, further comprising:

an alignment processor receiving a succession of images, the alignment processor identifying one or more landmarks in each received image, each successive received image having a coordinate system defined by landmarks identified in previously received images; wherein the diagnostic imaging processor determines the diagnostic imaging coordinate system by a process comprising sending the base sparse scout image and the one or more reformatted images to the alignment processor, each successive reformatted image being constructed by the reformatting processor using a corresponding coordinate system defined by landmarks previously identified by the alignment processor in the base sparse scout image or preceding reformatted images.

17. The diagnostic imaging system as set forth in claim 16, wherein the determining of a diagnostic imaging coordinate system further comprises:

causing the graphical user interface to display the reformatted images generated by the diagnostic imaging processor with corresponding landmarks superimposed thereon; and receiving an indication of whether the associated user approves of the diagnostic image coordinate system via the graphical user interface.

18. The method as set forth in claim 17, wherein responsive to the associated user not approving the diagnostic image coordinate system the determining of a diagnostic imaging coordinate system further comprises:

receiving a corrected landmark replacing one of the superimposed landmarks from the associated user via the graphical user interface.

19. The diagnostic imaging system as set forth in claim 17, wherein responsive to the associated user not approving the diagnostic image coordinate system the determining of a diagnostic imaging coordinate system further comprises:

causing the graphical user interface to display one of the base sparse scout image and one of the reformatted images to the associated user;

receiving an indication of one or more corrected landmarks from the associated user via the graphical user interface; and causing the reformatting processor to generate a corrected reformatted image having a corrected diagnostic imaging coordinate system defined at least by the one or more corrected landmarks.

20. A diagnostic imaging system comprising:

a processor storing: a software algorithm or routine for causing a magnetic resonance imaging scanner to acquire a base sparse scout image of an organ of interest in a standard coordinate system;

a software algorithm or routine for causing a processor to reformat the base sparse scout image to generate one or more reformatted images in coordinate systems other than the standard coordinate system;

a software algorithm or routine for causing the processor to determine a diagnostic imaging coordinate system aligned with the organ of interest using the base sparse scout image and the one or more reformatted images;

a graphical user interface for displaying acquired images and reformatted images to an associated user; and a software algorithm or routine for causing the magnetic resonance imaging scanner to acquire one or more diagnostic images of the organ of interest in the diagnostic imaging coordinate system.

* * * * *